United States Patent
Gühring et al.

(10) Patent No.: US 8,897,519 B2
(45) Date of Patent: Nov. 25, 2014

(54) SYSTEM AND METHOD FOR BACKGROUND PHASE CORRECTION FOR PHASE CONTRAST FLOW IMAGES

(75) Inventors: Jens Gühring, Erlangen (DE); Marie-Pierre Jolly, Hillsborough, NJ (US); Hui Xue, Franklin Park, NJ (US)

(73) Assignee: Siemens Aktiengesellschaft, Munich (DE)

( * ) Notice: Subject to any disclaimer, the term of this patent is extended or adjusted under 35 U.S.C. 154(b) by 614 days.

(21) Appl. No.: 13/210,497

(22) Filed: Aug. 16, 2011

(65) Prior Publication Data

US 2012/0076380 A1 Mar. 29, 2012

Related U.S. Application Data

(60) Provisional application No. 61/387,187, filed on Sep. 28, 2010.

(51) Int. Cl.
| | |
|---|---|
| *G06K 9/00* | (2006.01) |
| *G01R 33/563* | (2006.01) |
| *A61B 5/026* | (2006.01) |
| *A61B 5/055* | (2006.01) |
| *G01R 33/56* | (2006.01) |

(52) U.S. Cl.
CPC ........ *G01R 33/56316* (2013.01); *A61B 5/0263* (2013.01); *A61B 5/055* (2013.01); *G01R 33/5608* (2013.01)
USPC .......................................... 382/128; 382/173

(58) Field of Classification Search
CPC .......................... G06T 7/0012; G06K 2209/01
USPC ........... 382/111, 128, 131, 154; 600/410, 420
See application file for complete search history.

(56) References Cited

U.S. PATENT DOCUMENTS

| | | | | |
|---|---|---|---|---|
| 5,273,040 | A  * | 12/1993 | Apicella et al. | 600/410 |
| 7,065,242 | B2 * | 6/2006 | Petrov et al. | 382/154 |
| 7,515,742 | B2 * | 4/2009 | Zhao et al. | 382/128 |
| 7,660,461 | B2 * | 2/2010 | Lundstrom et al. | 382/168 |
| 8,055,051 | B2 * | 11/2011 | Sun et al. | 382/131 |
| 8,068,655 | B2 * | 11/2011 | Odry et al. | 382/131 |
| 8,160,305 | B2 * | 4/2012 | Laurint et al. | 382/111 |
| 8,218,848 | B2 * | 7/2012 | Lenglet et al. | 382/131 |
| 2008/0102453 | A1 * | 5/2008 | Ghosh et al. | 435/6 |
| 2011/0208039 | A1 * | 8/2011 | Guehring et al. | 600/410 |
| 2012/0078085 | A1 * | 3/2012 | Xue et al. | 600/420 |

OTHER PUBLICATIONS

Walker, PG, et al., "Semiautomated method for noise reduction and background phase error correction in MR phase velocity data," J. Magn. Reson. Imaging, 3:521-530, 1993.*

(Continued)

*Primary Examiner* — Vikkram Bali
*Assistant Examiner* — Xuemei Chen

(57) ABSTRACT

A method for correcting the background phase in magnetic resonance phase contrast flow images includes providing a time series of velocity encoded magnetic resonance images of a patient, where the time series of velocity encoded images comprises for each time point a phase contrast image where a pixel intensity is proportional to a flow velocity, measuring a change of intensity for each pixel over the time series of phase contrast images, identifying pixels with a low measure of temporal change as stationary pixels, and calculating a correction field for the stationary pixels, where the correction field represents a background phase to be subtracted from the phase contrast image.

16 Claims, 8 Drawing Sheets

(56) References Cited

OTHER PUBLICATIONS

Jan-Willem Lankhaar, et al., "Correction of Phase Offset Errors in Main Pulmonary Artery Flow Quantification," Journal of Magnetic Resonance Images 22: 73-79 (2005).

Hui Xue, et al., "Unsupervised Inline Analysis of Cardiac Perfusion MRI," MICCAI 2009, Part II, LNCS 5762, pp. 741-749, 2009.

* cited by examiner

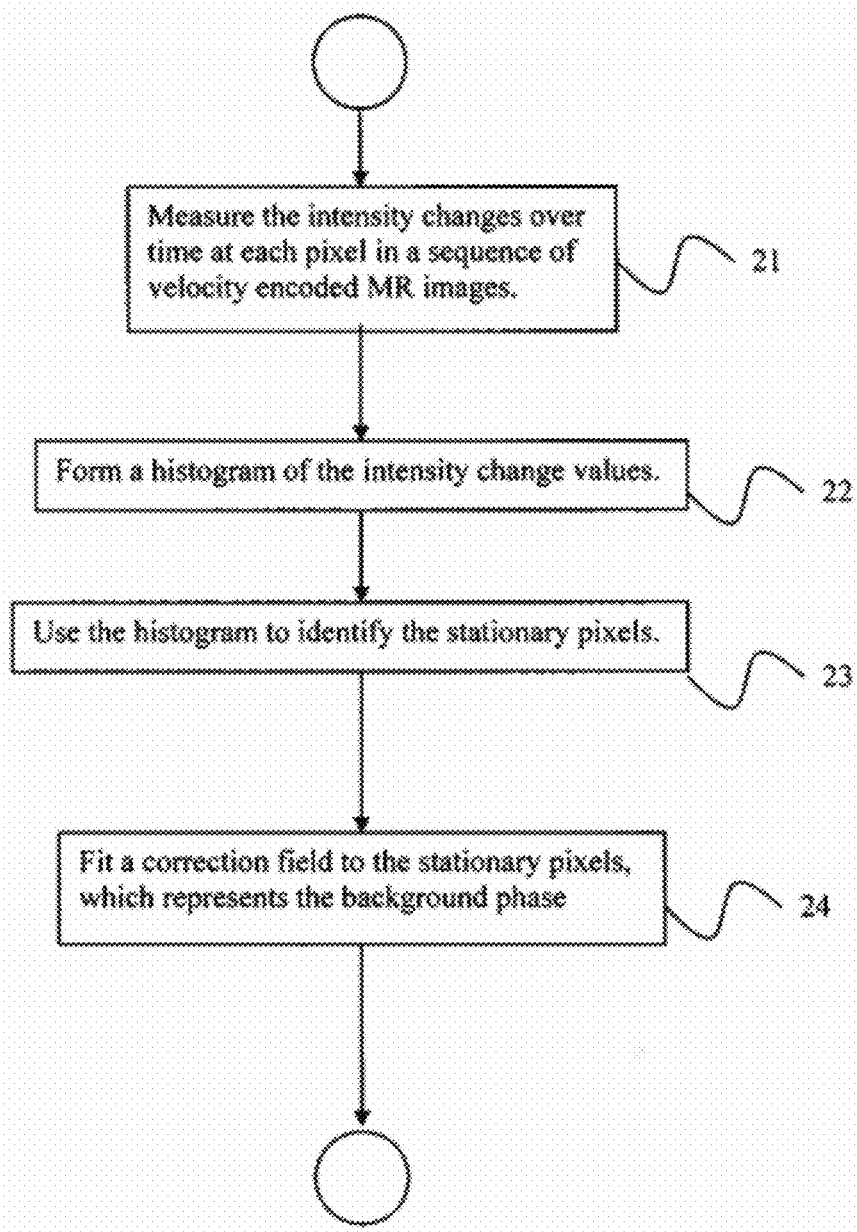

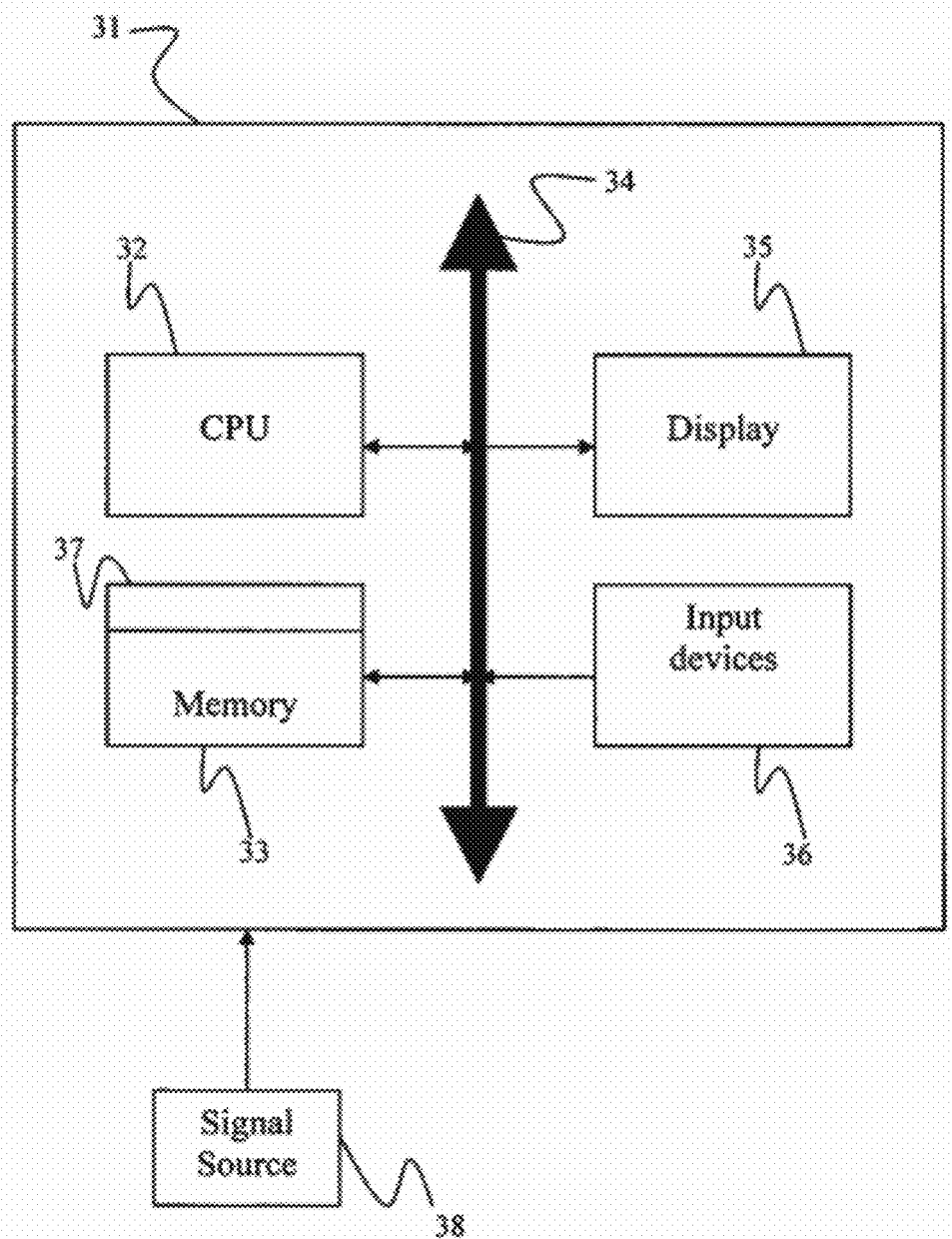

SYSTEM AND METHOD FOR BACKGROUND PHASE CORRECTION FOR PHASE CONTRAST FLOW IMAGES

CROSS REFERENCE TO RELATED UNITED STATES APPLICATIONS

This application claims priority from "Background Phase Correction For Phase Contrast Flow Images", U.S. Provisional Application No. 61/387,187 of Guehring, et al., filed Sep. 28, 2010, the contents of which are herein incorporated by reference in their entirety.

TECHNICAL FIELD

This disclosure is directed to methods for correcting background phase in phase contrast magnetic resonance images.

DISCUSSION OF THE RELATED ART

Phase contrast cardiovascular magnetic resonance imaging (MRI) sequences are used to measure blood flow velocity in vessels or at the heart valves. Velocity encoded MRI is based on detection of changes in the phase of proton precession. These changes are proportional to the velocity of the movement of those protons through a magnetic field with a known gradient. When using velocity encoded MRI, the result of the MRI scan is usually two sets of images for each time point in the cardiac cycle: an anatomical image and a phase contrast image where the signal intensity in each pixel is directly proportional to the velocity of a fluid flowing in the image. Note, however, that velocity encoded MRI can be performed using only the phase contrast images. The average velocity in a vessel is quantified by measuring the average signal intensity of the pixels in the cross section of the vessel, and then multiplying by a known constant. The flow is calculated by multiplying the mean velocity by the cross-sectional area of the vessel. This flow data can be used to graph flow versus time. The area under the flow versus time curve for one cardiac cycle is the stroke volume. MRI is typically used to quantify the flow over one cardiac cycle as the average of several heart beats, but it is also possible to quantify the stroke volume in real time on a beat-for-beat basis. This flow can be used to calculate cardiac output, shunt flow, and aortic or pulmonary regurgitation.

However, the velocity-encoded phase images should be corrected for velocity offset errors that occur during image acquisition. These errors are due to non compensated eddy-current-induced fields and concomitant gradient terms present in MR systems. As volume flow assessment in large vessels in determined by integration over time and space, relatively small velocity offsets can lead to significant errors in mean volume flow, stroke volume, and cardiac output.

In some cardiovascular MRI machines, a single reference region may be defined by the user to delineate stationary tissue and measure the background phase. It is assumed that the background phase in the vessel region will be identical. Therefore, the background phase of the reference region can be subtracted from the flow curve calculated from the vessel region. The challenge with this solution is that it is now known that the background is not uniform throughout the region and should not be estimated from a single reference region.

A more recent approach includes fitting a surface through the stationary pixels in the image. The stationary pixels are determined by calculating the variance over time of the gray levels at each pixels and choosing a predetermined percentage $\lambda$ of pixels with lowest variance. The surface is then approximated by a two dimensional Taylor expansion of order k. Published results for this approach suggest that the best results were obtained for $\lambda=25\%$ and $k=1$. However, the stationary pixels are chosen arbitrarily, independent of the sequence.

SUMMARY OF THE INVENTION

Exemplary embodiments of the invention as described herein generally include methods and systems for adaptively determining stationary pixels based on the sequence, and fitting a surface through the stationary pixels.

According to an aspect of the invention, there is provided a method for correcting the background phase in magnetic resonance phase contrast flow images, including providing a time series of velocity encoded magnetic resonance images of a patient, where the time series of velocity encoded images comprises for each time point a phase contrast image where a pixel intensity is proportional to a flow velocity; measuring, for each pixel, a change of intensity over the time series of phase contrast images; identifying pixels with a low measure of temporal change as stationary pixels; and calculating a correction field for the stationary pixels, where the correction field represents a background phase to be subtracted from the phase contrast image.

According to a further aspect of the invention, the correction field is a planar surface determined by a least squares fit to the stationary points.

According to a further aspect of the invention, the correction field is a free-form surface.

According to a further aspect of the invention, the free-form surface is determined by calculating a 2D tensor of uniform 1D cubic B-splines, $$T_{local}(x, y) = \sum_{m=0}^{3}\sum_{n=0}^{3} B_m(u)B_n(v)\varphi_{p+m,q+n},$$

where (x, y) is the coordinate of pixel i, the image $\Omega=\{(x, y)|0 \le x \le X, 0 \le y \le Y\}$ is represented by a sparse control point lattice $\phi_{p,q}$ having uniform grid spacing $\Delta_x$ and $\Delta_y$ in x and y directions, respectively, (x, y) is the coordinate of pixel i, $p=\lfloor x/\Delta_x \rfloor-1, q=\lfloor y/\Delta_y \rfloor-1, u=x/\Delta_x-\lfloor x/\Delta_x \rfloor$, and $v=y/\Delta_y-\lfloor y/\Delta_y \rfloor$, and $B_m$ represents an m-th basis function of the B-spline.

According to a further aspect of the invention, measuring a change of intensity for each pixel over the time series of phase contrast images comprises computing, for each pixel, an intensity variance over time series of phase contrast images.

According to a further aspect of the invention, identifying pixels with a low measure of temporal change comprises forming a histogram of intensity changes of all pixels, and determining from the histogram a threshold, where pixels whose intensity change is less than the threshold are considered as stationary pixel, and pixels whose intensity change is greater than the threshold are considered as moving pixels.

According to a further aspect of the invention, the background phase surface is calculated for an average phase contrast image that is an average over the time series of phase contrast images.

According to a further aspect of the invention, the method includes providing a time series of anatomical images, measuring, for each pixel, a change of intensity over the time series of anatomical images, normalizing the intensity change over the phase contrast images and the intensity change over the anatomical images, and selecting, for each pixel, the maximum of the intensity change over the phase contrast images and the intensity change over the anatomical images as the measure of temporal change for each pixel.

According to a further aspect of the invention, the method includes grouping neighboring stationary pixels together, and removing small and ill-shaped groups of pixels from the stationary pixels.

According to another aspect of the invention, there is provided a program storage device readable by a computer, tangibly embodying a program of instructions executable by the computer to perform the method steps for correcting the background phase in magnetic resonance phase contrast flow images.

BRIEF DESCRIPTION OF THE DRAWINGS

FIG. 2 is a flowchart of an algorithm to extract stationary pixels from a phase contrast image, according to an embodiment of the invention.

FIG. 3 is a block diagram of an exemplary computer system for implementing a method for correcting background phase in phase contrast magnetic resonance (MR) images, according to an embodiment of the invention.

DETAILED DESCRIPTION OF EXEMPLARY EMBODIMENTS

Figure 1A:
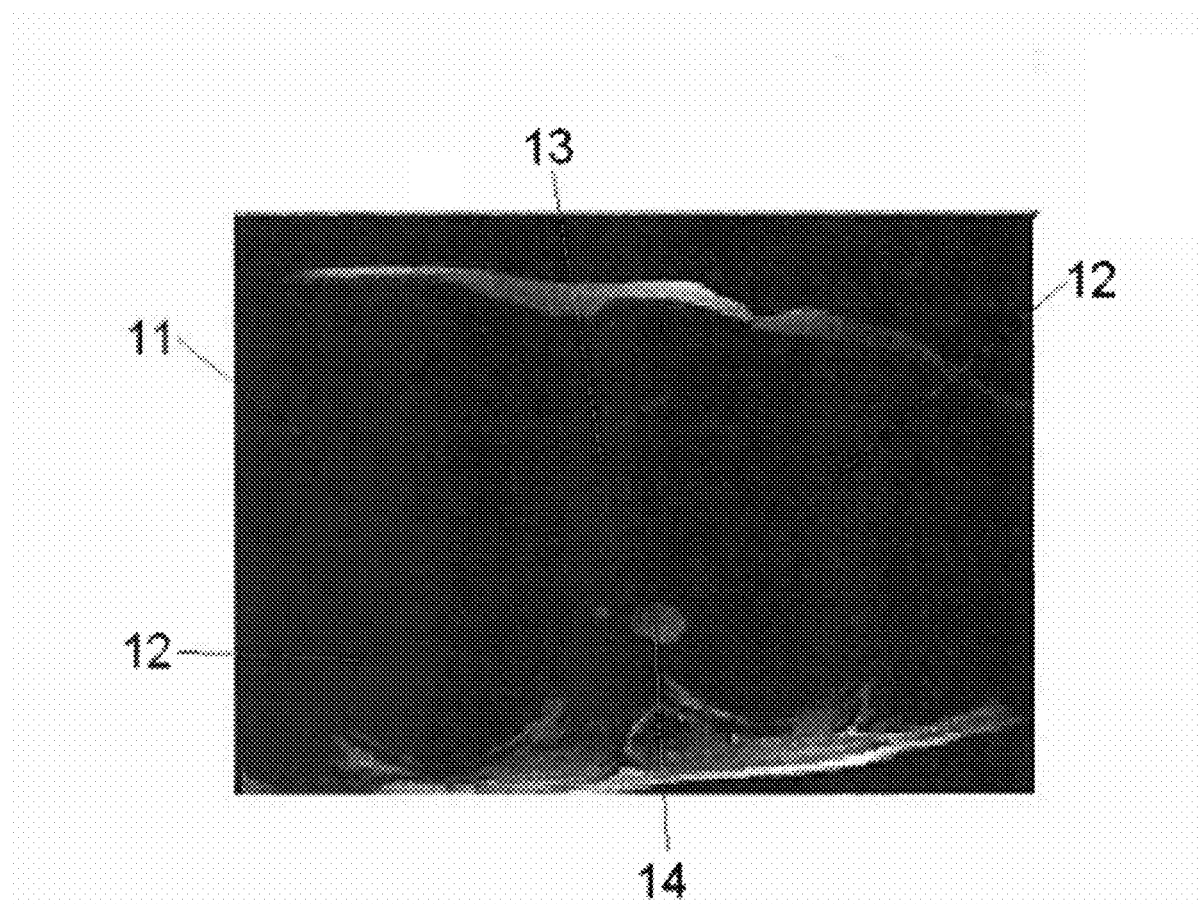
FIGS. 1(a)-(f) illustrate an algorithm to extract stationary pixels from a phase contrast image, according to an embodiment of the invention

Exemplary embodiments of the invention as described herein generally include systems and methods for correcting background phase in phase contrast magnetic resonance (MR) images. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-dimensional images and voxels for 3-dimensional images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the inventions are not limited to such images, and can be applied to images of any dimension, e.g., a 2-dimensional picture or a 3-dimensional volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Figure 1B:
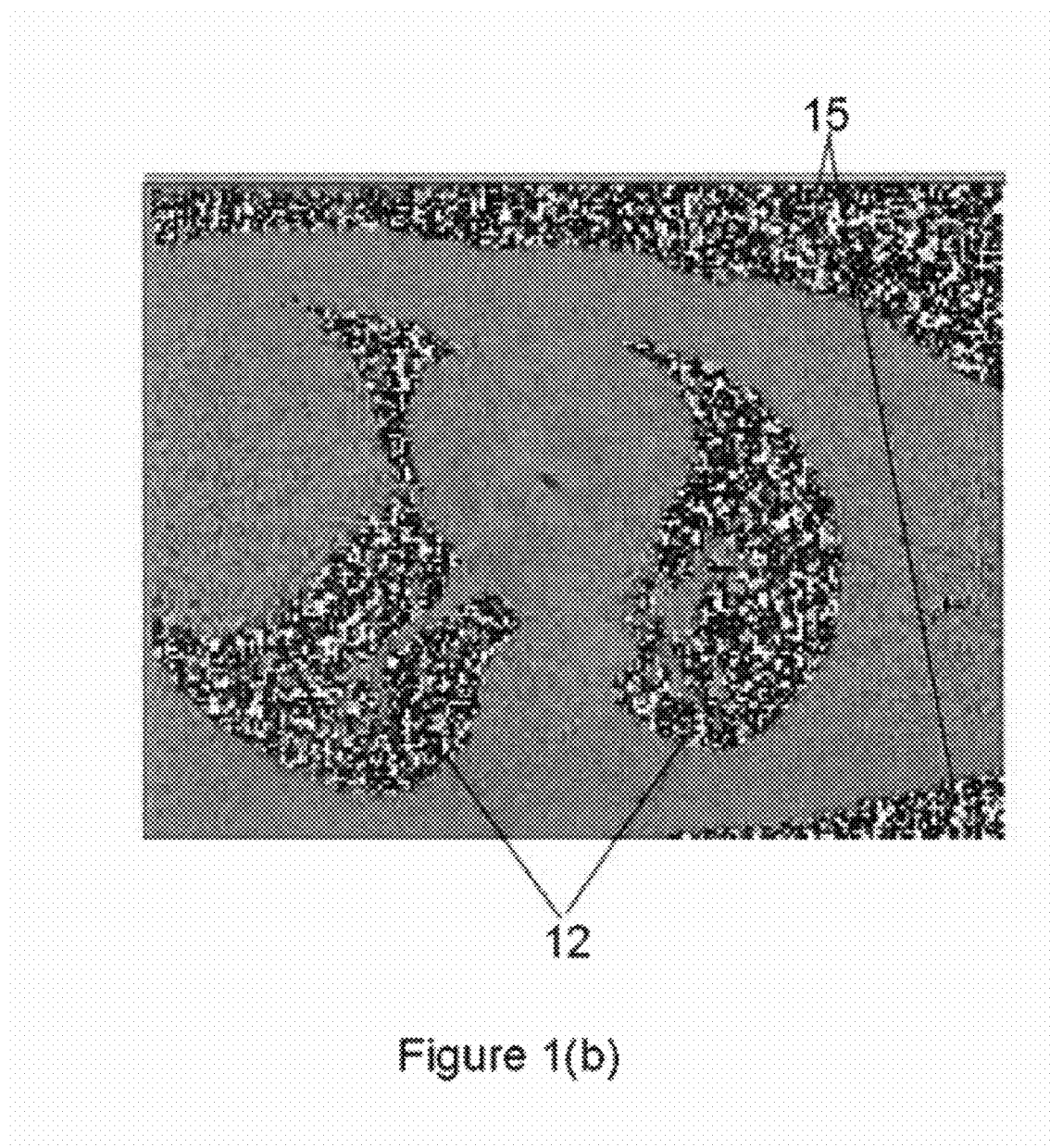

An algorithm according to an embodiment of the invention to extract stationary pixels from a phase contrast image is illustrated by FIGS. 1(a)-(f), and by the flowchart of FIG. 2. FIG. 1(a) depicts an original magnitude image, with a liver 11, lungs 12, aortic valve 13, and descending aorta 14, and FIG. 1(b) depicts an original phase contrast image, each selected from a sequence of velocity encoded MR images of a heart. The same reference numbers refer to the same item in FIGS. 1(a)-(f). Referring to FIG. 1(b), the salt and pepper regions 15 and 12 respectively correspond to outside air and the lungs, which contain air. Phase contrast MRI cannot measure velocity in air, thus air shows up as noise in these images.

Figure 1C:
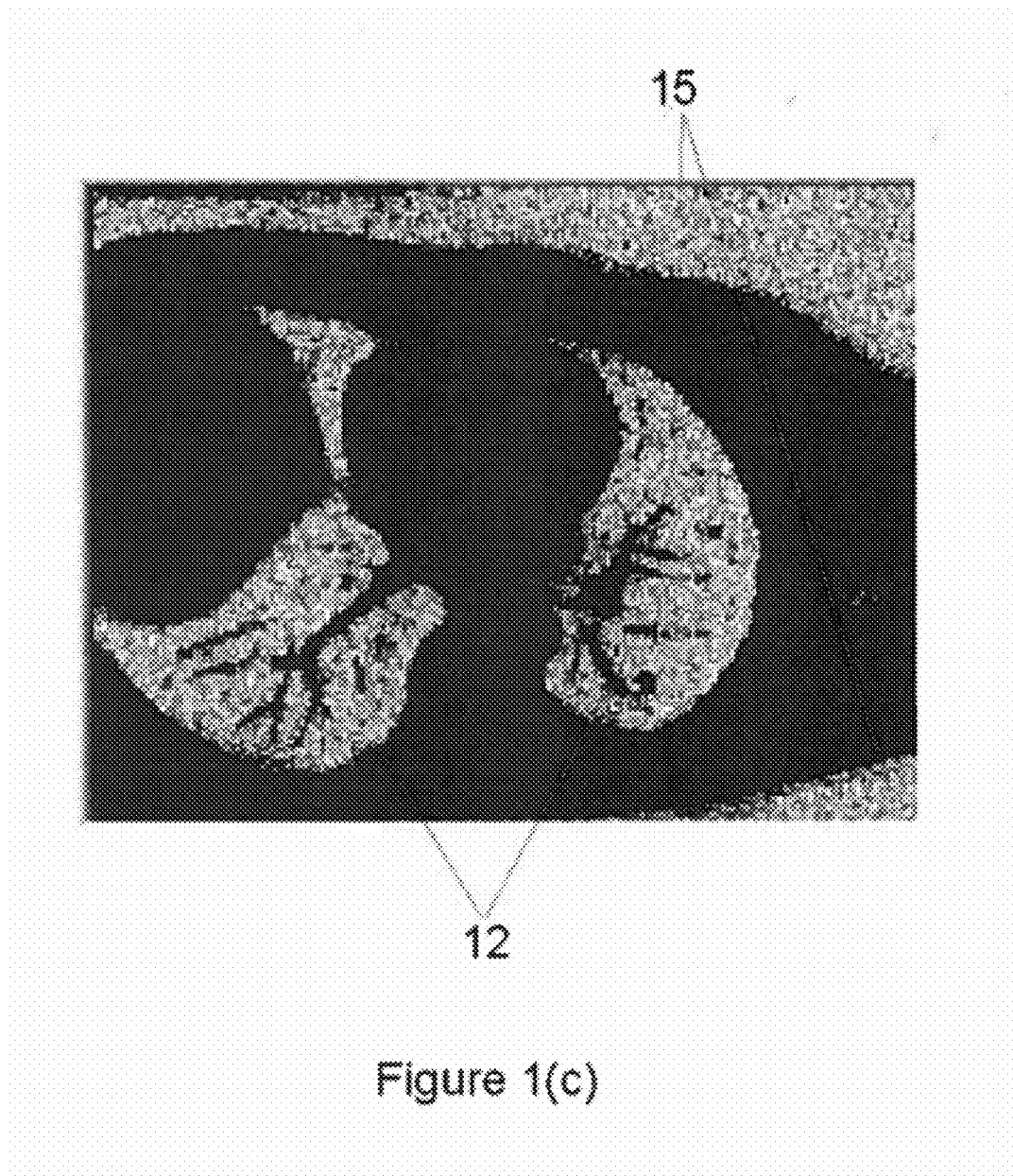

Referring now to FIG. 2, given a sequence of velocity encoded MR images, an algorithm according to an embodiment of the invention begins at step 21 by determining the change of pixel intensity levels over time at each pixel in the sequence of velocity encoded MR images, illustrated in FIG. 1(c). According to some embodiments of the invention, only a series of phase contrast is provided. According to other embodiments of the invention, both a time series of anatomical magnitude images and a time series of phase contrast images are provided. According to an embodiment of the invention, the change of pixel intensity levels is represented by the intensity variance of each pixel over the time series of images. According to some embodiments of the invention, only a series of phase contrast images is provided, in which case the variance is calculated over the series of phase contrast images. According to other embodiments of the invention, if both anatomical magnitude images and phase contrast images are provided, the variance is computed over time as the maximum of the variance over time of the magnitude images and the variance over time of the phase contrast images at each pixel, after a suitable normalization.

Figure 1D:
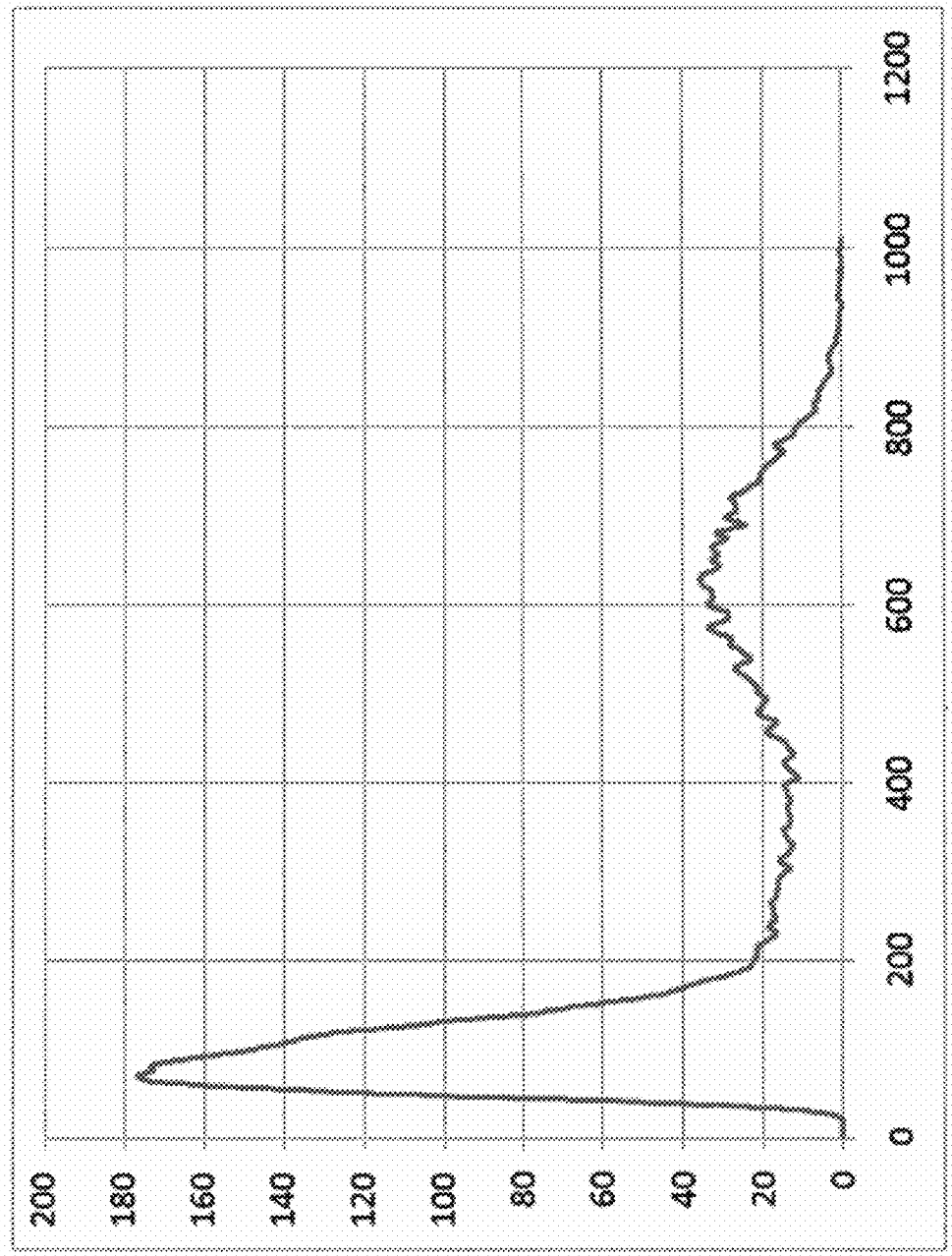
Figure 1E:
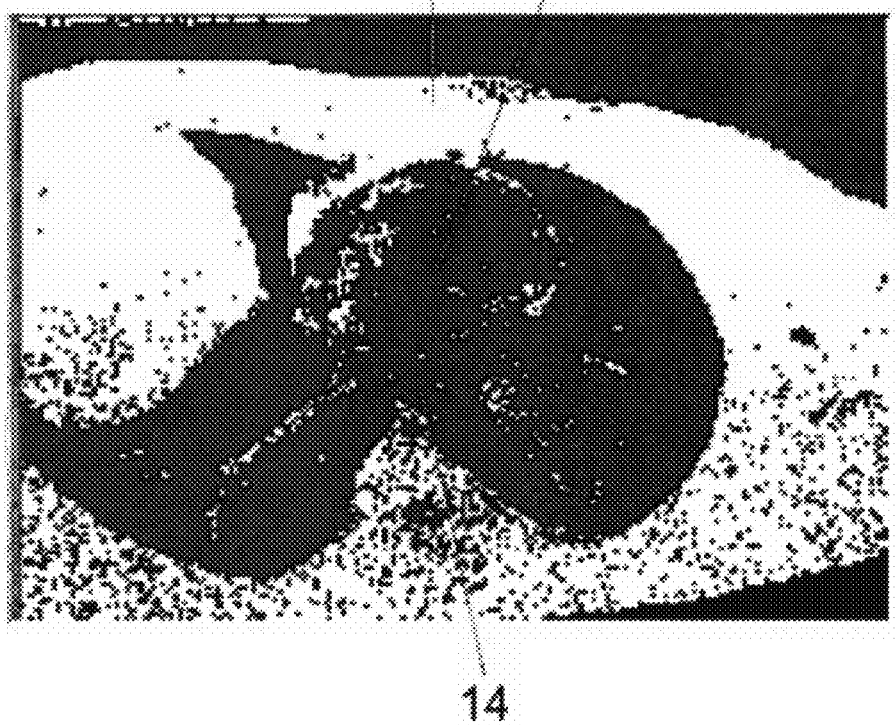
Figure 1F:
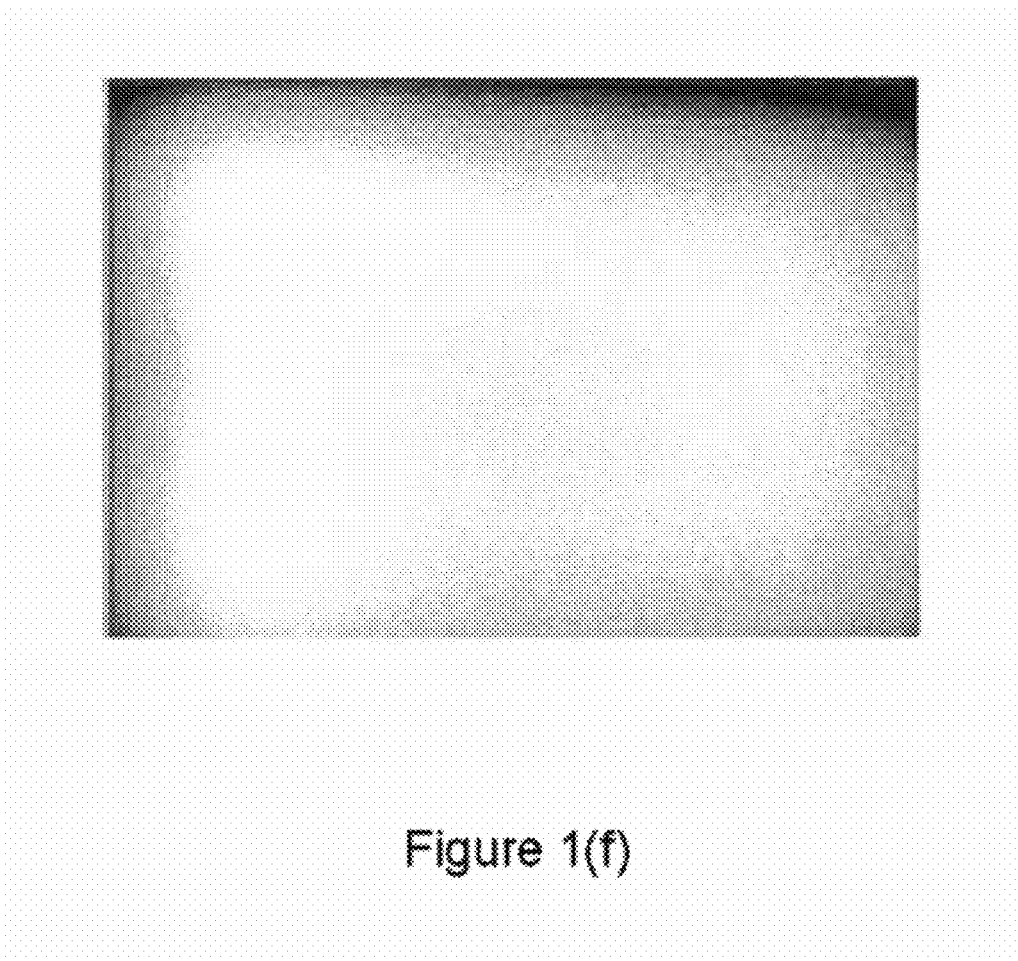

Next, at step 22, the variances are analyzed to determine a threshold that separates the stationary pixels from the moving pixels. According to embodiments of the invention, a histogram is formed of the variance values. The histogram includes two peaks: one for the noisy background and air with a large variance and another peak for tissue with a smaller variance. The histogram, depicted in FIG. 1(d), shows the number of pixels with a certain variance on the y-axis for all possible variances on the x-axis. One looks for the 2 peaks, separated by a valley, in that histogram. Only the first peak, closest to the origin with the largest variances, is of interest. At step 23, a Gaussian mode is fit to first peak in the histogram, from which the mean d standard deviation (stddev) of the first peak in the histogram are computed. According to embodiments of the invention, the mean and standard deviation are used to determine a threshold. Exemplary, non-limiting thresholds definitions include: (1) Mean+n×StdDev, where n>1; (2) the variance for which the value of the histogram is half the peak value; and (3) the larger of the two previous values. Exemplary, non-limiting values for n are 2 and 3. According to other embodiments of the invention, the threshold may be determined from a pre-selected percentage of the difference between a variance minimum and a variance maximum. Any pixel with a variance less than that threshold is considered a stationary pixel. All the pixels beyond the right tail of that mode are considered to be moving pixels. FIG. 1(e) shows the mask formed by the stationary pixels. Notice how the descending aorta 14 and aortic valve 13 are not part of the stationary pixels. Then at step 24, a correction field is fit through the stationary pixels of an average phase contrast image over time. This correction field, which represents the background phase, is shown in FIG. 1(f).

In an additional optional step, neighboring stationary pixels can be grouped to together to improve spatial coherence. There may be holes, etc., in the groups, as long there exists a neighbor, such as 4- or 8-neighbor that is classified to be stationary as well. An exemplary, non-limiting algorithm for performing this grouping is a connected-component labeling algorithm. Once the groups are formed, small or very ill-shaped groups, such as very thin groups, can be removed, as they will likely not reliably contribute to the determination of the background region due to their potentially random nature and limited spatial resolution.

The simplest correction field to fit to the stationary pixels is a plane. This can be done using a least squares fit, which is equivalent to finding the eigenvalues and eigenvectors of the points in 3D and setting the normal of the plane to the eigenvector with smallest eigenvalue and a point on the plane to the center of mass of the points.

A free-form surface can also be fit to the stationary pixels to represent the correction field. A B-Spline freeform surface may be applied to approximate the bias field. In this representation, a dense 2D bias field is parameterized on a sparse control point lattice. The image is represented as $\Omega = \{(x, y) | 0 \le x \le X, 0 \le y \le Y\}$ and $\phi$ represents a grid of control points $\phi_{p,q}$ with the grid spacing being $\Delta_x \times \Delta_y$. This spacing between adjacent control points is uniform for each coordinate direction. A 2D tensor of uniform 1D cubic B-splines may be defined as follows:

$$T_{local}(x, y) = \sum_{m=0}^{3} \sum_{n=0}^{3} B_m(u) B_n(v) \varphi_{p+m,q+n}$$

where (x, y) is the coordinate of pixel i, $p = \lfloor x/\Delta_x \rfloor - 1$, $q = \lfloor y/\Delta_y \rfloor - 1$, $u = x/\Delta_x - \lfloor x/\Delta_x \rfloor$, and $v = y/\Delta_y - \lfloor y/\Delta_y \rfloor$. $B_m$ represents the m-th basis function of the B-spline. The basis functions of cubic B-splines have limited support. Therefore changing a control point in the grid affects only a 4×4 region around that control point.

$T_{local}(x, y)$ is computed for all pixels in the image, including pixel positions belonging to moving and stationary. The input to compute $T_{local}(x, y)$ are the phase values for all stationary pixels. The output of $T_{local}(x, y)$ is a smoothing correction field for every pixel in the image. For a pixel location $(x_1, y_1)$ belonging to a stationary pixel, $T_{local}(x_1, y_1)$ is a smoothing approximation of the background phase value at location $(x_1, y_1)$. For a pixel location $(x_2, y_2)$ belonging to a moving pixel, the phase value is initially unknown. Thus, $T_{local}(x_2, y_2)$ is computed and treated as an estimation of background phase value of $(x_2, y_2)$.

So, the effect of computing $T_{local}(x, y)$ is to obtain a dense pixel-wise phase image for both stationary and moving pixels, given the phase values of the stationary pixels as the input. The properties of a bspline ensure that $T_{local}(x, y)$ is smooth across the image region. For a pixel (x, y) that is stationary, $T_{local}(x, y)$ will not in general equal the original phase value. This is reasonable, as the original phase values of stationary pixels include noise and phase changes coming from real tissue, while the background phase should be smooth and slowly changing. By computing a smoothing approximation of stationary phase values, the embedded components corresponding to background phase can be extracted.

A method according to an embodiment of the invention should produce good results for the following two reasons. First, the stationary pixels are not chosen arbitrarily using a fixed threshold, but rather using a threshold that depends on the images themselves. Second a free form surface fitting algorithm according to an embodiment of the invention has already been used successfully for cardiac perfusion surface coil correction in other settings.

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

FIG. 3 is a block diagram of an exemplary computer system for implementing a method for correcting background phase in phase contrast magnetic resonance (MR) images, according to an embodiment of the invention. Referring now to FIG. 3, a computer system 31 for implementing the present invention can comprise, inter alia, a central processing unit (CPU) 32, a memory 33 and an input/output (I/O) interface 34. The computer system 31 is generally coupled through the I/O interface 34 to a display 35 and various input devices 36 such as a mouse and a keyboard. The support circuits can include circuits such as cache, power supplies, clock circuits, and a communication bus. The memory 33 can include random access memory (RAM), read only memory (ROM), disk drive, tape drive, etc., or a combinations thereof. The present invention can be implemented as a routine 37 that is stored in memory 33 and executed by the CPU 32 to process the signal from the signal source 38. As such, the computer system 31 is a general purpose computer system that becomes a specific purpose computer system when executing the routine 37 of the present invention.

The computer system 31 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to exemplary embodiments, those skilled in the art will appreciate that various modifications and substitutions can be made thereto without departing from the spirit and scope of the invention as set forth in the appended claims.

What is claimed is:

1. A method for correcting the background phase in magnetic resonance phase contrast flow images, the method comprising the steps of:

providing a time series of anatomical magnetic resonance images and velocity encoded magnetic resonance images of a patient, wherein said time series of velocity encoded images comprises for each time point a phase contrast image wherein a pixel intensity is proportional to a flow velocity;

computing, for each pixel, an intensity variance over the time series of phase contrast images and an intensity variance over the time series of anatomical images;

selecting, for each pixel, the maximum of the intensity variance over the phase contrast images and the intensity variance over the anatomical images as a measure of temporal variance for each pixel;

forming a histogram of the intensity variance of all pixels;

determining a threshold from said histogram, wherein pixels whose intensity change is less than the threshold are considered as stationary pixels, and pixels whose intensity change is greater than the threshold are considered as moving pixels; and calculating a correction field for the stationary pixels, wherein said correction field represents a background phase to be subtracted from the phase contrast image.

2. The method of claim 1, wherein said correction field is a planar surface determined by a least squares fit to the stationary points.

3. The method of claim 1, wherein said correction field is a free-form surface.

4. The method of claim 3, wherein said free-form surface is determined by calculating a 2D tensor of uniform 1D cubic B-splines, $$T_{local}(x, y) = \sum_{m=0}^{3} \sum_{n=0}^{3} B_m(u) B_n(v) \varphi_{p+m,q+n},$$

wherein (x, y) is a pixel coordinate, said image $\Omega=\{(x, y)|0 \leq x \leq X, 0 \leq y \leq Y\}$ is represented by a sparse control point lattice $\phi_{p,q}$ having uniform grid spacing $\Delta_x$ and $\Delta_y$ in x and y directions, respectively, $p=\lfloor x/\Delta_x \rfloor -1$, $q=\lfloor y/\Delta_y \rfloor -1$, $u=x/\Delta_x - \lfloor x/\Delta_x \rfloor$, and $v=y/\Delta_y - \lfloor y/\Delta_y \rfloor$, and $B_m$ represents an m-th basis function of the B-spline.

5. The method of claim 1, wherein the background phase surface is calculated for an average phase contrast image that is an average over the time series of phase contrast images.

6. The method of claim 1, further comprising
normalizing the intensity change over the phase contrast images and the intensity change over the anatomical images.

7. The method of claim 1, further comprising:
grouping neighboring stationary pixels together; and
removing small and ill-shaped groups of pixels from the stationary pixels.

8. The method of claim 1, wherein determining a threshold from said histogram further comprises fitting a Gaussian model to a histogram peak closest to the origin and determining a mean and standard deviation of said Gaussian model, wherein the mean and standard deviation are used to determine a threshold.

9. A non-transitory computer readable program storage device, embodying a program of instructions executable by a computer to perform method steps for correcting the background phase in magnetic resonance phase contrast flow images, the method comprising the steps of:

providing a time series of anatomical magnetic resonance images and velocity encoded magnetic resonance images of a patient, wherein said time series of velocity encoded images comprises for each time point a phase contrast image wherein a pixel intensity is proportional to a flow velocity;

computing, for each pixel, an intensity variance over the time series of phase contrast images and an intensity variance over the time series of anatomical images;

selecting, for each pixel, the maximum of the intensity change over the phase contrast images and the intensity change over the anatomical images as the measure of temporal change for each pixel;

forming a histogram of the intensity variance of all pixels;

determining a threshold from said histogram, wherein pixels whose intensity change is less than the threshold are considered as stationary pixels, and pixels whose intensity change is greater than the threshold are considered as moving pixels; and calculating a correction field for the stationary pixels, wherein said correction field represents a background phase to be subtracted from the phase contrast image.

10. The computer readable program storage device of claim 9, wherein said correction field is a planar surface determined by a least squares fit to the stationary points.

11. The computer readable program storage device of claim 9, wherein said correction field is a free-form surface.

12. The computer readable program storage device of claim 11, wherein said free-form surface is determined by calculating a 2D tensor of uniform 1D cubic B-splines, $$T_{local}(x, y) = \sum_{m=0}^{3} \sum_{n=0}^{3} B_m(u) B_n(v) \varphi_{p+m,q+n},$$

wherein (x, y) is a pixel coordinate, said image $\Omega=\{(x, y)|0 \leq x \leq X, 0 \leq y \leq Y\}$ is represented by a sparse control point lattice $\phi_{p,q}$ having uniform grid spacing $\Delta_x$ and $\Delta_y$ in x and y directions, respectively, $p=\lfloor x/\Delta_x \rfloor -1$, $q=\lfloor y/\Delta_y \rfloor -1$, $u=x/\Delta_x - \lfloor x/\Delta_x \rfloor$, and $v=y/\Delta_y - \lfloor y/\Delta_y \rfloor$, and $B_m$ represents an m-th basis function of the B-spline.

13. The computer readable program storage device of claim 9, wherein the background phase surface is calculated for an average phase contrast image that is an average over the time series of phase contrast images.

14. The computer readable program storage device of claim 9, the method further comprising
normalizing the intensity change over the phase contrast images and the intensity change over the anatomical images.

15. The computer readable program storage device of claim 9, the method further comprising:
grouping neighboring stationary pixels together; and
removing small and ill-shaped groups of pixels from the stationary pixels.

16. The computer readable program storage device of claim 9, wherein determining a threshold from said histogram further comprises fitting a Gaussian model to a histogram peak closest to the origin and determining a mean and standard deviation of said Gaussian model, wherein the mean and standard deviation are used to determine a threshold.

* * * * *